United States Patent [19]

Malen et al.

[11] 4,154,851

[45] May 15, 1979

[54] BENZYLAMINO ALKANOIC ACID DERIVATIVES, USING COMPOSITIONS CONTAINING THE SAME, AND METHODS FOR UTILIZING SAID DERIVATIVES AND COMPOSITIONS

[75] Inventors: Charles Malen, Fresnes; Pierre Roger, Saint-Cloud; Jean-Claude Poignant, Bures sur Yvette, all of France

[73] Assignee: Science Union et Cie, Societe Francaise de Recherche Medicale, Suresnes, France

[21] Appl. No.: 776,893

[22] Filed: Mar. 11, 1977

Related U.S. Application Data

[63] Continuation-in-part of Ser. No. 610,943, Sep. 8, 1975, abandoned.

[30] Foreign Application Priority Data

Mar. 11, 1976 [GB] United Kingdom ............... 09782/76

[51] Int. Cl.$^2$ ................. A01K 31/135; C07C 101/00; C07C 87/00
[52] U.S. Cl. .................................... 424/318; 260/404; 260/404.5
[58] Field of Search .......... 260/404, 404.5 R, 404.5 F, 260/404.5 CN; 424/318

[56] References Cited

U.S. PATENT DOCUMENTS

| | | | |
|---|---|---|---|
| 3,740,439 | 6/1973 | Eichenberger | 424/319 |
| 3,758,528 | 9/1973 | Malen et al. | 260/404 |
| 3,883,586 | 5/1975 | Yokoyama et al. | 260/404 |

OTHER PUBLICATIONS

Wagner et al., Synthetic Organic Chemistry, John Wiley & Sons, N.Y., N.Y., 1953, pp. 662–663.

*Primary Examiner*—Allen B. Curtis
*Attorney, Agent, or Firm*—Omri M. Behr

[57] ABSTRACT

This invention relates to novel ω-benzylamino alkanoic acids, to their salts with an organic or mineral base or with an organic or mineral acid. These alkanoic acids may be in a racemic form or resolved into their optically-active enantiomers.

They are produced by condensing an oxoalkanoic acid with a benzylamine under reducing conditions.

This invention also relates to ω-benzylamino alkanoic amides and to ω-benzylamino alkanoic acid esters.

They have therapeutical use, namely in the psychotherapeutical field. They are utilized in the form of pharmaceutical compositions.

16 Claims, No Drawings

BENZYLAMINO ALKANOIC ACID DERIVATIVES, USING COMPOSITIONS CONTAINING THE SAME, AND METHODS FOR UTILIZING SAID DERIVATIVES AND COMPOSITIONS

The present application is a continuation in part of our previous U.S. patent application Ser. No. 610,943 filed Sept. 8, 1975, now abandoned.

PRIOR ART

The prior art may be illustrated with U.S. Pat. No. 3,758,528 (to the same assignee)

Suter — U.S. Pat. No. 3,691,196
Kruger — U.S. Pat. No. 3,712,924
Felder — U.S. Pat. No. 3,576,854
Eichenberger — U.S. Pat. No. 3,740,439
Beregi — U.S. Pat. No. 3,856,857
Beregi — U.S. Pat. No. 3,759,979
Galler — U.S. Pat. No. 2,813,118
Parry — U.S. Pat. No. 3,956,370

These references are cited to show the state of the art for analogous compounds. However, the claims are deemed patentable thereover.

SUMMARY OF THE INVENTION

The present invention relates to novel ω-benzylamino alkanoic acids and their derivatives having the formula I

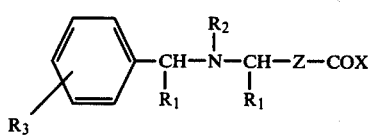

wherein $R_1$ represents a lower alkyl radical having from 3 to 6 carbon atoms in a straight or branched chain, $R_2$ and $R_4$ represent a hydrogen atom or a lower alkyl radical having from 1 to 5 carbon atoms in a straight or branched chain, $R_3$ represents a hydrogen atom, a lower alkoxy radical or a trifluoromethyl radical or a halogen atom, a trifluoromethoxy, acetylamino, sulfamido, lower alkylamino sulphonyl, dilower alkylamino sulphonyl, cyano or an acyl group from a lower alkyl carboxylic acid, Z is an alkylene group from 4 to 10 carbon atoms in straight or branched chain, and X is a hydroxy, a phenoxy, a lower alkoxy or an amino group of the formula

in which each of R and R' is a hydrogen atom or a lower alkyl, lower alkenyl, phenyl-lower alkyl or phenyl group or R and R' together form an alkylene chain having from 2 to 6 carbon atoms which may be interrupted by one or two heteroatoms.

Among the compounds of the invention it may be particularly cited the compounds of formula I'

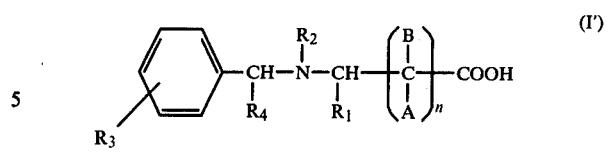

in which $R_3$, $R_4$, $R_1$ and $R_2$ have the above given definitions and

A and B, which may be the same or different, each represents a hydrogen atom, a methyl radical or an ethyl radical, and n is an integer from 4 to 10;

the compounds of formula $I_B$

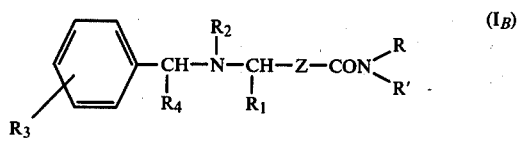

in which the definitions of the substituents remain unaltered;

the compounds of formula $I_C$

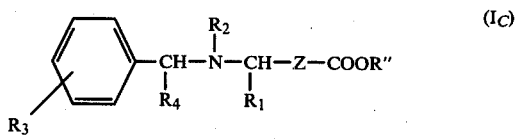

in which $R_1$, $R_2$, $R_3$, $R_4$ and Z have the meanings given above, and R" is a lower alkyl group, a substituted lower alkyl group, a phenyl group or a substituted phenyl group.

The present invention also relates to the salts of a compound of the formula I with a mineral or organic base or acid.

The alkanoic chain of a compound of the formula I include at least an asymmetric carbon atom and therefore may exist in a racemic form or, if necessary after having been resolved, for example by means of an optically-active organic base or an optically-active organic acid, in an optically-active form.

The compounds of general formula I and the salts thereof are endowed with interesting pharmacological and therapeutical properties. They exert an anti-agressive activity without having other affects on the central nervous system. They thus have a therapeutical use in human or veterinary medicine for the treatment of psychic depression associated with a state of anxiety.

Accordingly, the present invention also provides a pharmaceutical preparation containing a compound of the general formula I, or a physiologically tolerable salt thereof, in admixture or conjunction with a pharmaceutically acceptable carrier, such as magnesium carbonate, magnesium stearate, water, sugar, talc, cocoa butter or sodium chloride solutions.

The present invention relates also to a process for preparing compounds of formula I which consists in condensing an alkanoic acid of the formula

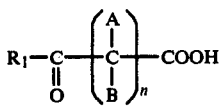

with a benzylamine of the formula

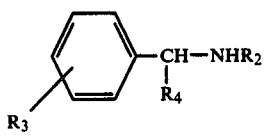

in which $R_2$, $R_3$ and $R_4$ are either a hydrogen atom or a substituent, under reducing conditions and recovering the desired acid which may, when necessary, resolved into its optically-active enantiomers or salified with a base or an acid, or converted into the corresponding ester or amide.

PREFERRED EMBODIMENTS

This invention related to amino-carboxylic acids, to their esters and to the corresponding amides.

According to the present invention there are provided new ω-benzylamino alkanoic derivatives of the formula I

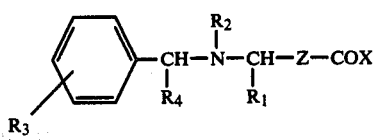

wherein
- $R_1$ represents a lower alkyl radical having from 3 to 6 carbon atoms in a straight or branched chain,
- $R_2$ and $R_4$ represent a hydrogen atom or a lower alkyl radical having from 1 to 5 carbon atoms in a straight or branched chain,
- $R_3$ represents a hydrogen atom, a lower alkoxy radical a trifluoromethyl radical, a halogen atom, trifluoromethoxy, acetylamino, sulfamido, lower alkyl aminosulphonyl, di(lower alkyl) amino sulphonyl, cyano or lower acyl group
- Z is an alkylene group having from 4 to 10 carbon atoms in straight or branched chain,
- and X is a hydroxy, a lower alkoxy, a phenoxy or an amino radical of the formula

in which each R and R' is a hydrogen, a lower alkyl, a lower alkenyl, a phenyl lower alkyl, a phenyl group or R and R' together are an alkylene chain of 2 to 6 carbon atoms which may be interrupted by one or two heteroatoms.

The alkanoic chain of a compound of the formula I may include at least an asymmetric carbon atom and therefore may exist in a racemic form or, if necessary after having been resolved, for example by means of an optically-active organic base or an optically-active organic acid, in an optically-active from.

The present invention also provides a salt of a compound of the general formula I with a mineral or organic base or acid.

As salts with acids there are preferred those with a strong acid, for example hydrochloric acid, sulphuric acid or formic acid. There may also be mentioned salts with optically-active acids.

When X is a hydroxy, it may also be salified with a base.

As mineral base salts, there may be especially mentioned, for example, those of alkali metals, for example sodium salts, potassium salts and lithium salts, ammonium salts, those of earth-alkali metals, aluminum salts, iron (II) salts and magnesium salts.

As organic base salts, there may be especially mentioned, for example, those with a primary, secondary or tertiary lower alkylamine, for example, ethylamine, triethylamine and diisobutylamine, those with a substituted lower alkyl amine, for example aminoethanol and 3-dimethylamino propanol-1, those with a lower alkylene diamine, for example ethylenediamine those with an arylamine, for example α-naphthylamine, o.anisidine and p.phenetidine, those with an aryl lower alkylamine, for example phenylethyl amine and α-methylbenzylamine, those with a quaternary ammonium base, a guanidino base such as, glyocyamine or agmatine and those with an amino acid, for example, glycine, alanine, β-alanine, lysine, proline and nor-valine.

Among the compounds of general formula I, there may be cited as preferred compounds:

the benzylamino alkanoic acid of the general formula $I_A$

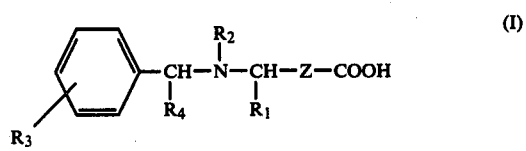

in which
- $R_1$ is an alkyl group having from 3 to 6 carbon atoms,
- each of $R_2$ and $R_4$ is a hydrogen atom or a lower alkyl group,
- $R_3$ is a hydrogen atom, a halogen atom or a lower alkoxy, trifluoromethyl, trifluoromethoxy, acetylamino, sulfamido, lower alkylaminosulphonyl, dilower alkylaminosulphonyl, cyano or lower acyl group,
- Z is alkylene of 4 to 10 carbon atoms, any one of said carbon atoms being substituted by one or two members of the group consisting of methyl and ethyl.

more specifically the compounds of formula I'

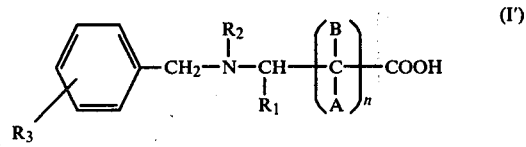

wherein
- $R_1$ represents a lower alkyl radical having from 3 to 6 carbon atoms in a straight or branched chain,
- $R_2$ represents a hydrogen atom or a lower alkyl radical having from 1 to 5 carbon atoms in a straight or branched chain, $R_3$ represents a hydrogen atom, a lower alkoxy radical or a trifluoromethyl radical or a halogen atom, A and B, which may be the same or different, each represents a hydrogen atom, a methyl radical or an ethyl radical, and n is an integer from 4 to 10 and namely dl 7-(p.fluorobenzylamino) 9-methyldecanoic acid and its optically-active isomers, dl 7-(p.fluorobenzylamino) 10-methylundecanoic acid, dl 7-(p.fluorobenzylamino) 9,9-dimethyldecanoic acid, dl 7-(p.fluorobenzylamino) 8-methylnonanoic acid.

They may also be cited the following compounds:

dl 4,4-dimethyl 7-(p.fluorobenzylamino) 8-methylnonanoic acid, dl 8-(p.fluorobenzylamino) 9-methyl decanoic acid, dl 9-(p.fluorobenzylamino) 10-methyl undecanoic acid, dl 2,8-dimethyl 7-(p.fluorobenzylamino) nonanoic acid.

Among the compounds of general formula I or of formula I' the racemic form is less active than one of the optically-active forms and more precisely than the dextrorotatory isomer.

Instead of the free acid, the base or acid addition salts thereof may also be of interest. The most interesting are those with a therapeutically-compatible mineral or organic base or with a therapeutically-compatible mineral or organic acid.

The salts with a base or an acid which cannot be used in therapy, may however be used as a mean for identification, purification, separation or resolution. The chloroplatinates, perchlorates, periodates, bis naphtylphosphonates, d-NN dimethyl tartramates may be used for such purposes. The addition salt with brucine, strychine or quinine may also be used as a separation or resolution agent.

They are also of interest the ω-benzylamino-alkanoic acid amides of the formula $I_b$

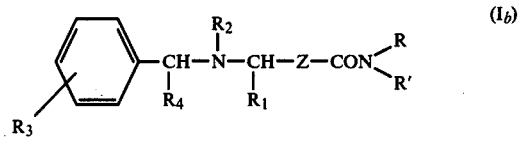

in which $R_1$ is an alkyl group having from 3 to 6 carbon atoms, each of $R_2$ and $R_4$ is a hydrogen atom or a lower alkyl group, $R_3$ is a hydrogen atom, a halogen atom or a lower alkoxy, trifluoromethyl, trifluoromethoxy, acetylamino, sulfamido, lower alkylaminosulphonyl, dilower alkylaminosulphonyl, cyano or lower acyl group, Z is an alkylene group having from 4 to 10 carbon atoms in straight or branched chain, and each of R and R' is a hydrogen atom or a lower alkyl, lower alkenyl, phenyl-lower alkyl or phenyl group or R and R' together form an alkylene chain having from 2 to 6 carbon atoms which may be interrupted by one or two hereroatoms, and precisely dl 6-[p.fluorobenzylamino]-7-methyl-N-methyloctanamide, dl 6-[p.fluorobenzylamino]-7-methyl-N,N-dimethyloctanamide, dl 7-[p.fluorobenzylamino]-8-methylnonanamide.

They are also of interest the esters of the formula $I_c$

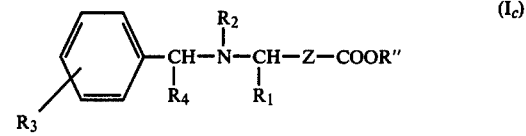

in which $R_1$, $R_2$, $R_3$, $R_4$ and Z have the meanings given above, and R" is a lower alkyl group, a substituted lower alkyl group, a phenyl group or a substituted phenyl-group.

The substituent $R_1$ is preferably a branched chain alkyl radical, for example an iso-propyl radical, a tert-butyl radical an iso-butyl radical, or an iso-pentyl radical.

The lower alkoxy radical contains from 1 to 5 carbon atoms in straight or branched-chain.

The substituent $R_3$ may be located in any position of the phenyl ring, but is preferably in the para position to the methyl amino grouping. When $R_3$ is a halogen atom, it is preferably a fluorine atom. It may, however, be a chlorine, bromine or iodine atom. When $R_3$ is a lower alkoxy it may be a methoxy, ethoxy, isopropoxy, isobutoxy or diethylaminoethoxy.

The compounds of general formula I and the salts there are endowed with interesting pharmacological and therapeutical properties. They exert an anti-aggressive activity without having other effects on the central nervous system. They thus have a therapeutical use in human or veterinary medicine for the treatment of psychic depression associated with a state of anxiety. The therapeutical properties of the compounds of general formula I may be explained through a functional activation of the somatic sensory nervous system (somaesthesic pathway). The mode of action of these compounds is somewhat like that found with the Thyrotropin Releasing Hormon (TRH). As described by E. Wei in Nature 253 (1975) 739, TRH injected in the brain of the previously anaesthetized rat at the level of the lateral thalamic and hypothalamic zones induces a tremoring effect quite similar to that caused by the compounds of general formula I.

The site of action of the compounds of general formula I thus appears to be quite similar to that of TRH as mentioned in this literature.

Their therapeutic use as anti-aggressive agent without any depressive or stimulating effect is based on the stimulating effect on the EEG and a TRH like neuronal stimulating effect. Their mode of action is therefrom quite different from that of any known anti-depressive or any anti-anxiety agent.

Accordingly, the present invention also provides a pharmaceutical preparation containing a compound of the general formula I, or a physiologically tolerable salt thereof, in admixture or conjunction with a pharmaceutically acceptable carrier, such as magnesium carbonate, magnesium stearate, water, sugar, talc, cocoa butter or sodium chloride solutions.

The preparation should be in a form suitable for administration by the parenteral, oral or rectal route. There may be especially mentioned injectable solutions or suspensions packed in ampouls, phials, multi-dosis flasks or auto-injectible syringes, tablets, coated tablets, granulates, capsules, drinkable suspensions or syrups or suppositories containing from 10 to 500 mg of active ingredient.

The daily dose may widely vary, depending on the therapeutical use, the age and the weight of the patient. It may, for example, range from 50 mg to 2000 mg a day, in the man divided into one to four administrations.

The present invention also provides a process for producing the acids of general formula $I_A$ and the salts thereof. More particularly, compounds of formula $I_A$ may be obtained by condensing an oxoalkanoic acid of the general formula II

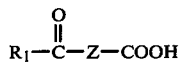 (II)

wherein $R_1$ and Z have the meanings given above with a benzylamine of the general formula III.

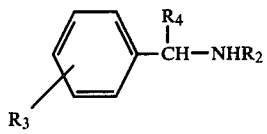 (III)

wherein $R_2$, $R_3$ and $R_4$ have the meanings given above, and reducing the keto group adjacent the radical $R_1$. If desired, a salt of a compound of the general formula $I_A$ may be prepared by addition thereto of a mineral or organic base or acid. Compounds of formula $I_A$ may, if desired, be resolved into their optical isomers by means of an optically-active base or an optically-active organic acid.

Preferably, the said keto group is reduced by carrying out the condensation under reducing conditions, for example hydrogenating conditions in the presence of an hydrogenation catalyst. The catalyst is usually a metal or a derivative of a metal belonging to the platinum family, for example platinum, platinum oxides, platinum salts, palladium irridium, rhodium or rhenium. The reducing conditions may also be afforded by using a mixed alkalimetal hydride, for example sodium borohydride, lithium borohydride, potassium borohydride or lithium aluminohydride. The reducing conditions may be generated in situ or introduced into the reaction mixture after condensation has taken place.

The present invention also provides a process for producing an oxo-alkanoic acid of the general formula II which comprises submitting a cyclic β-diketone of general formula IV.

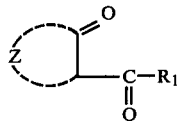 (IV)

wherein Z and $R_1$ have the above-given meanings to alkaline splitting and recovering the corresponding oxo-alkanoic acid.

Preferably, the splitting is effected by means of a strong alkali-metal base, for example sodium hydroxide, potassium hydroxide or lithium hydroxide.

There may be especially mentioned a process for producing $R_1$ - oxo alkanoic acids of the formule II'

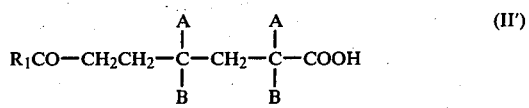 (II')

in which the substituents $R_1$, A and B have the above-given meanings, which comprises submitting a cyclohexanone of the formula IV'

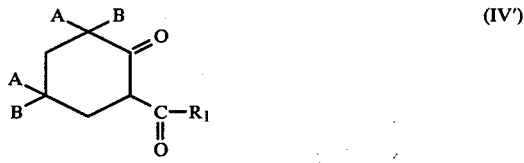 (IV')

to alkaline splitting and recovering the desired β-oxo alkanoic acid

The cyclic β-diketones of general formula IV' may be obtained by condensing a cycloalkenylamine of formula V

 (V)

wherein A, B and n have the meanings given above and X and Y, which may be the same or different, each represents a lower alkyl radical or a phenyl radical or together form with the nitrogen atom to which they are bonded the alkylene chain of a nitrogenous saturated heterocycle, the ring of which may contain another hetero-atom, with a functional derivative of an organic carboxylic acid of the formula VI

$R_1$—CO—W (VI)

in which $R_1$ has the meanings given above and W is a halogen atom or a $R_1$ COO radical.

The condensation of the compound of the formula V and the derivative of the formula VI may be carried out in the presence of a catalyst, for example a Lewis acid, for example aluminum chloride or boron trifluoride.

Preferably, the compounds of the formula V are those in which X and Y together represent a cyclic structure, for example a pyrrolidino or a piperidino or a morpholino radical.

The starting keto alkanoic acid of the general formula II may also be obtained according to a process which consists in esterifying a dicarbocyclic acid of the formula

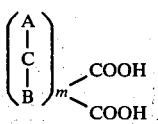

in which n is an integer of 4 to 10 to produce a dialkyl ester thereof, selectively saponifying the latter to produce the monoalkyl ester of the formula

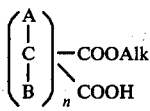

in which A, B and n are defined as above, submitting the latter to the action of a halogenating agent to produce an acid halide of the formula

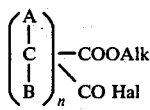

in which
Hal is a halogen atom
Alk means an alkyl radical
A, B and n are defined as above
condensing this halide with an organo-cadmium derivative of the formula $R_1$—Cd—T in which $R_1$ has the above-given definitions and T is an anion, to produce a keto alkyl ester of the formula

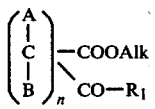

in which the meanings of the substituents A, B, Alk, $R_1$ and n remain unaltered
which is finally saponified in alkaline medium to produce aketo alkanoic acid of the formula II.

The present invention also provides a process for preparing the amides of general formula $I_B$ which comprises reacting an ω-benzylamino alkanoic acid of the formula $I_A$

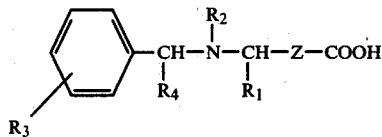

in which $R_1$, $R_2$, $R_3$, $R_4$ and Z have the meanings given above, or a functional derivative thereof, with a compound of the formula VII.

in which R and R' have the meanings given above.

The resulting amide may be salified by adding a mineral or organic acid, preferably a strong acid, or when desired, resolved into its optically active isomers by salification with an optionally active carboxylic, sulphonic or phosphoric acid.

The amidation step may be performed using an acid of formula $I_A$ alone or in the presence of dehydrating agent such as ethoxyacetylene, carbonyl-diimidazole or a dicycloalkyl-or a dialkyl-carbodiimide. The amidation step may also be performed in the presence of a metallic salt, such as cupric chloride or ferric chloride, which may facilitate the condensation.

The amidation step may also be performed by producing a functional derivative of the acid of general formula $I_A$ in situ. It may thus be convenient to generate a methyl ester by reacting the acid with a solution of diazomethane in methylene chloride, expelling excess reagent and reacting the resulting methyl ester with the compound of formula VII. It may also be convenient to produce the acid halide by reacting the acid of general formula $I_A$ with an halogenating agent such as thionyl chloride or sulphuryl chloride in a polar medium such as hexamethylphosphoramide or dimethylsulphone. The functional derivative may also be a mixed halide such as that formed by reaction of the carboxylic acid with an alkyl-halo formate in the presence of a tri-loweralkylamine, for example ethyl chloro- or bromoformate in the presence of triethylamine. The functional derivative may also be a lower alkyl ester of the acid of general formula $I_A$, for example an ethyl ester, an isopropyl ester or a pentyl ester. It may further be an aryl ester for example a phenyl ester, a chlorophenyl ester or a nitrophenyl ester. The amidation step is usually carried out in this case in the presence of a basic agent such as sodium methylate, sodamide, lithium dialkylamide or potassium tert-butylate.

The present invention also provides esters of the acids of general formula $I_C$, that is to say compounds of the formula

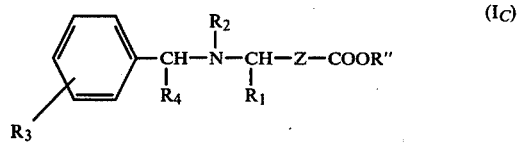

wherein the substituents $R_3$, $R_4$, $R_2$, $R_1$, Z and R'' have the above-given definitions.

These esters are conveniently prepared by reacting an alkali-metal salt of an acid of general formula $I_C$ with an appropriate halide, for example a chloride or a bromide, or by reacting the free acid with an alkanol in an acidic medium.

The term "substituted lower alkyl group" is used herein to designate a lower alkyl group bearing one or more substituents such as a hydroxy, a lower alkoxy, a lower acyloxy, a dilower-alkylamino group, a pyridyl-lowr alkyl, a morpholinyl-lower alkyl, a furyl-lower alkyl, a (N-ethyl pyrrolidinyl-2)-methyl group, an isopropylidenedioxypropyl group or a β-glyceryl group. Examples of such substituted lower alkyl groups are dimethylaminopropyl, β-ethoxyethoxy, methoxymethyl, ribityl ($HOCH_2(CHOH)_3CH_2$—), pentaerithrityl and butane-2,3-diol groups.

These esters may exist in racemic form or may be resolved into their optically active isomers. They may be resolved by salification with an optically-active organic acid or, preferably after debenzylation by catlytic hydrogenation, salification of the free amino group with an optically-active organic acid. After resolution, the optically-active isomer is condensed with a phenyl alkyl ketone of the formula

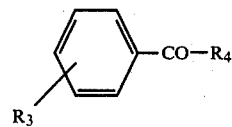

in which $R_3$ and $R_4$ have the meanings given above, under reducing conditions, such as catalytic hydrogenation, in order to produce the desired optically-active ester.

The esters of formula $I_C$ are useful intermediates for preparing the amides of formula $I_B$. They may also be used as medicines in the form of pharmaceutical compositions in admixture or conjunction with a pharmaceutically suitable carrier.

For the acids of formula $I_A$ the resolution step may be performed either on the final compound of formula $I_A$ or on an intermediate step. Preferably the resolution step is performed after esterification then hydrogenolysis of the final product, on the resulting amino compound of the formula VIII

wherein
R, $R_1$, Z have the above-given meanings
and Alk is an alkyl radical.

The resolution is preferably carried out by salification with an optically-active acid such as di-tartaric acid, dibenzoyl d-tartartic acid, d-camphoric acid or abietic acid.

The resolution may also be performed by salification of the aminoacid of formula IX

with an optically-active base.

Useful bases are by example l-ephedrine, brucine, quinine, spartenine or 2-dimethylamino 1-p. nitrophenyl propane 1,3-diol.

In both processes the resolved salt is further separated and hydrolysed. The optically-active resulting said or ester is then condensed with a benzaldehyde or phenyl lower alkyl ketone under reducing and when necessary alkaline conditions.

The starting benzylamines of the general formula III are disclosed in the literature and may be obtained, according to known methods, namely by condensing the corresponding benzaldehyde or the corresponding phenyl alkyl ketone with an alkylamine of the formula $R_2 NH_2$ in the presence of a hydrogenation agent.

The following examples illustrate the invention.
The indicated temperatures are expressed in degrees Centigrade.

EXAMPLE 1
7- p. fluorobenzylamino 10- methyl undecanoic acid

Step A—1- morpholino cyclohex-1 ene 295g of cyclohexanone and 261 g of morpholine are dissolved in 800ml of benzene. After the whole has been dissolved, 1.5g of p. toluene sulphonic acid are added and the mixture is heated under reflux. The water formed is extracted continuously by azeotropic distillation. After 20 hours reflux, the remaining solvent is distilled off and the oily residue is recovered. 379 g of the enamine are so obtained, boiling under 2mm at 115° to 117°. The yield amounts to 76%.

The pure 1- morpholino cyclohex - 1 ene has a refractive index of $N_D^{22} = 1.5122$.

Step B — 2— (4'- methyl valeryl) cyclohexanone

To solution of 16.7g 1-morpholino cyclohex -1 ene in 45 ml chloroform, 10.1g of triethylamine are added. Over a period of one hour a solution of 13.4g of isocaproyl chloride in 15 ml chloroform is added, with stirring.

The mixture is stirred for two hours at room temperature and is thereafter heated at 60° for 3 hours. It is kept aside for a night, then 150 ml hydrochloric acid are added. The mixture is shaken and is then allowed to settle. The chloroformic phase is discarded. The aqueous phase is partially neutralized with sodium carbonate until the ph value reaches 6 and is then extracted with chloroform three times. The organic phases are united, washed with water, dried over sodium sulphate, filtered and evaporated to dryness.

The crude residue weighing 20.1g, is purified by distillation under reduced pressure, 10.3g of the pure cyclohexanone are recovered (Yield 55%).

2-(4'-methyl valeryl) cyclohexanone is a liquid boiling under 0.3mm at 96 to 100°.

$N_D^{25} = 1.4895$

| Analysis $C_{12} H_{20} O_2 = 196.28$ | | |
|---|---|---|
| | C% | H% |
| Calculated | 73.43 | 10.27 |
| Found | 72.91 | 10.13 |

Step C — 7- oxo 10- methyl undecanoic acid 10 g of 2-(4'-methyl valeryl) cyclohexanone are added to 70ml of a 5% aqueous solution of sodium hydroxide. The mixture is heated under reflux for 2 hours. The aqueous solution is then made acidic with a 4 N solution of hydrochloric acid and is extracted with ether. The ethereous phase is separated, is washed with a saturated solution of sodium chloride, is dried on sodium sulphate, is filtered and is evaporated to dryness. The solid residue weighing 9g is left to stand at room temperature. The crystallization begins quickly. The crystals are recovered and are recrystallized from n-pentane (yield 6.2g).

7- oxo 10- methyl undeanoic acid melts at 49° to 51°.

Step D — DL 7- fluorobenzylamino 10- methyl undecanoic acid

A fresh solution of 1.75 g of p. fluorobenzylamine and 1.4g methylamine is added to a solution of 3g 7- oxo 10-methyl undecanoic acid in 20 ml ethanol. The mixture is warmed at 40° for a night. 0.1g of platinum oxide is then added and the mixture is hydrogenated under ordinary pressure at 40°. After the theoretical amount of hydrogen has been absorbed, the catalyst is filtered off and the solvent is evaporated under reduced pressure. The oily residue crystallized quickly, at room temperature. 4.2g of crystals are recovered (yield 94%). The product is purified by recrystallizing it from 30 ml acetonitrile and is dried over phosphoric anhydride in a closed vessel. The yield is 3g.

7-(p. fluorobenzylamino) 10- methyl undecanoic acid is a crystalline solid melting at 84° to 85°.

| Analysis $C_{19} H_{30} FNO_2 = 323.44$ | | | |
|---|---|---|---|
| | C% | H% | N% |
| Calculated | 70.56 | 9.34 | 4.33 |
| Found | 70.36 | 9.1 | 4.47 |

-continued

| Analysis $C_{19} H_{30} FNO_2$ = 323.44 | | |
|---|---|---|
| C% | H% | N% |
| 70.70 | 9.12 | 4.42 |

7-(p. fluorobenzylamino) 10-methyl undecanoic acid may be salified by adding a stoichiometric amount of sodium carbonate and evaporating off the solvent.

EXAMPLE II to VIII dl 7-(para fluorobenzylamino) 9-methyl decanoic acid

Using the same procedure as described in Example 1 they have been successively obtained:
1-morpholinocyclohex 1-ene
2-(4'-methyl valeryl) cyclohexanone
{Bp.102.104/0.4mm
$n_D^{28}$ = 1,4930}-yield 60%
7-oxo 9-methyl decanoic acid
MP = 32°-36°-yield 83%
dl (7-p.fluorobenzylamino) 9-methyl decanoic acid
MP = 79°-83° (acetonitrile)

| Analysis $C_{18} H_{28} FNO_2$ = 309,41 | | | |
|---|---|---|---|
| | C | H | N% |
| Calculated | 69.87 | 9.12 | 4.53 |
| Found | 69.85 | 9.09 | 4.71 | dl 7-(para fluorobenzylamino) 8-methyl nonanoic acid

Using the same procedure as in example I, they have been obtained:
2(isobutyroyl) Cyclohexanone
7-oxo 8-methyl nonanoic acid
dl 7-(para fluorobenzylamino)8-methylnonanoic acid
MP = 88°-89° (ethyl acetate)

| Analysis $C_{17} H_{26} FNO_2$ = 294,38 | | | |
|---|---|---|---|
| | C | H | N% |
| Calculated | 69.39 | 8.56 | 4.76 |
| Found | 69.21 | 8.76 | 4.52 | dl 7-(parap fluorobenzylamino) 9,9-dimethyl decanoic acid

Using the same procedure as in example I, they have been obtained:
1-morpholinocyclohex 1-ene
2-(2-2-dimethyl 4-oxo butyl) cyclohexanone
BP 82–84/0.1mm (yield 61%)
$n_D^{23}$ = 1,4885
7-oxo 9-9-dimethyl decanoic acid
MP = 25°-26° (yield 80%)
dl 7-(para fluorobenzylamino) 9,9-dimethyl decanoic acid
MP = 63.65° (acetonitrile)

| Analysis $C_{19} H_{30} FNO_2$ = 323,44 | | | |
|---|---|---|---|
| | C | H | N% |
| Calculated | 70.56 | 9.34 | 4.33 |
| Found | 70.18 | 9.18 | 4.52 | dl 6-(para fluorobenzylamine) 7-methyl octanoic acid

Using the same procedure as in example I, they have been obtained:
1 morpholino cyclopent -1-enone
2-isobutyroyl cyclopentanone
BP = 98–100/13 mm (yield 56%)
$n_D^{23}$ = 1.4790
6-oxo 7-methyl octanoic acid
BP 124°-127°/0.05mm (yield 77%)
$n_D^{21}$ = 1.4460
dl 6(parafluorobenzylamino) 7-methyl octanoic acid

| Analysis $C_{16} H_{24} FNO_2$ = 281.36 | | | |
|---|---|---|---|
| | C | H | N% |
| Calculated | 68.30 | 8.60 | 4.98 |
| Found | 67.89 | 8.48 | 5.19 |
| MP = 109–115 (acetonitrile) | | | |

This compounds is soluble in N/10 hydrochloric acid solutions.

dl 4-4dimethyl 7-para fluorobenzylamino 8-methyl nonanoic acid

Using the same procedure as in example I, they have been obtained:
1-morpholino 4,4-dimethyl cyclohex-1 ene
2-isobutyroyl 4,4-dimethyl cyclohexanone
BP 76°-80°/0.1 mm (yield 40%)
$n_D^{23}$ = 1.4840
4,4-dimethyl 7-oxo S-methyl nonanoic acid
BP : 136°-140°/0.05 mm (yield 55%)
$n_D^{22}$ = 1.4550
dl 4,4-dimethyl 7-(para fluorobenzylamino) 8-methyl nonanoic acid
MP = 145.148° (methyl cellosolve)

| Analysis $C_{19} H_{30} FNO_2$ = 323,45 | | | |
|---|---|---|---|
| | C | H | N% |
| Calculated | 70.56 | 9.35 | 4.33 |
| Found | 70.42 | 9.21 | 4.52 | dl 7-(p. chlorobenzylamino) 8-methyl nonanoic acid

Using the procedure of example I, and using p-chloro-benzylamine as the starting material, the title compound is obtained with a :
MP = 79.85° (acetonitrile)

| Analysis $C_{17} H_{26} Cl NO_2$ = 311,84 | | | | |
|---|---|---|---|---|
| | C | H | N | Cl% |
| Calculated | 65.49 | 8.41 | 4.50 | 11.37 |
| Found | 65.56 | 8.35 | 4.81 | 11.06 |

This compound is soluble in N/10 hydrochloric acid solutions giving a weakly acid solution.

dl 7-(m-methoxybenzylamino) 8-methyl nonanoic acid

Using m-methoxybenzylamine as the starting material the title compound is obtained with a :
MP = 64°-67°

| Analysis $C_{18} H_{29} O_3 N$ = 307.23 | | | |
|---|---|---|---|
| | C | H | N% |
| Calculated | 70.30 | 9.51 | 4.55 |
| Found | 70.17 | 9.58 | 4.39 |

EXAMPLE 9

7-(p.fluorobenzylamino) 8-methyl nonanoic acid(laevo-rotatory isomer)

Step A

Starting from 240 g.dl 7-(p.fluorobenzylamino) 8-methyl nonanoic acid and ethanol in the presence of sulphuric acid at reflux temperature, 188.67 g. of ethyl ester of dl 7-(p.fluorobenzylamino) 8-methyl nonanoic acid are obtained the yield amounts to 67% - BP 142°-147°/0.01 mm.

Step B

In a flask 125 g. of ethyl ester of dl 7-(p.fluorobenzylamino) 8-methyl nonanoic acid are dissolved in 550 ml ethanol 8 g. of palladized charcoal are then introduced and the mixture is freed from atmospheric oxygen by bubbling nitrogen. The hydrogenation is thereafter performed at atmospheric pressure and heating at about 60° C. After one hour the theoretical amount of hydrogen has been absorbed and the catalyst is suction-filtered then washed with ethanol. The ethanolic filtrates are united, discoloured with charcoal, filtered and evaporated off, 92 g. of ethyl ester of dl 7-amino 8-methyl nonanoic acid are thus recovered. The raw product is further purified by fractional distillation — the yield amounts to 93%. The ethyl ester of 7-amino 8-methyl nonanoic acid is a liquid boiling at 84°-87°/0.01 mm $n_D^{20} = 1,4470$ protometric titration : 102±2%

Step C 60.5 g. of dl ethyl ester of 7-amino 8-methyl nonanoic acid are dissolved in 400 ml ethanol. To this solution 42 g. d(+) tartaric acid are added and thoroughly mixed. The crystallisation is initiated by scratching then kept for a night in a cool place. The crystalline mixture is separated by filtration and dried, then recrystallised from ethanol giving 26 g. of raw product melting at 100°-103°.

The rotatory power of the d(+) tartarate is $\{\alpha\}_{578}^{22} = + 20.4°$ (C=1% water)

$\{\alpha\}_{365}^{22} = + 47.9°$ (C=1% water)

optical purity as ascertained by VPC higher than 95%.

Step D

The dextro rotatory d(+) tartarate is converted into the base with sodium hydroxide hydro-ethanolic solution and after evaporation of the solvent 12.8 g of dextro-rotatory ethyl ester of 7-amino 8-methyl nonanoic acid are recovered BP = 85°-89°/0.05 mm $\{\alpha\}_{578}^{22} = + 14.7°$ (C=1% ethanol)

$\{\alpha\}_{365}^{22} = + 41.3°$ (C=1% ethanol)

Step E 10 g of dextro-rotatory ethyl ester of 7-amino 8-methyl nonanoic acid are dissolved in 50 ml ethanol and 12 g p.fluorobenzadelyde are added thereto. The mixture is heated to reflux for 1 h30 then let to revert to room temperature. 10 g triethylamine and 0.5 g platinum oxide are added and the whole mixture is hydrogenated at atmospheric pressure while heating at about 60° C. The hydrogenation is terminated when the theoretical amount of hydrogen has been absorbed. The catalyst is separated by filtration, washed many times with ethanol and the alcoholic filtrates united. The solvent is distilled off and a white crystalline mass is obtained. After recrystallisation from isopropyl ether a yeild of 89% of laevo rotatory ethyl ester of 7-(Para fluorobenzylamino) 8-methyl nonanoic acid is obtained — B.P.=128°-134°/0.02mm $\{\alpha\}_{578}^{22} = - 3.4°$ (C=1% ethanol)

$\{\alpha\}_{365}^{22} = - 16.3°$ (C=1% ethanol)

Similarly using instead of p.fluorobenzaldehyde m.methoxybenzaldehyde, p.chlorobenzaldehyde,m.trifluoromethyl benzaldehyde acetophenone or phenyl ethyl ketone they are obtained respectively laevo rotatory ethyl ester of 7-(m.methoxy benzylamino) 8-methylnonanoic, laevorotatory ethyl ester of 7-(p.chlorobenzylamino) 8-methylnonanoic acid, laevorotatory ethyl ester of 7-(m.trifluoromethyl benzylamino) 8-methyl nonanoic acid, laevorotatory ethyl ester of 7-($\alpha$-methyl benzylamino) 8-methyl nonanoic acid or laevorotatory ethyl ester of 7-($\alpha$-ethyl benzylamino) 8-methyl nonanoic acid.

Step F

6g2 laevorotatory ethyl ester of 7-(para fluorobenzylamino) 8-methyl nonanoic acid are dissolved in 25 ml ethanol. To the solution 100 ml of 2N solution of sodium hydroxide in ethanol are added and the whole mixture kept under stirring at about 10° C. for two hours. The reaction medium is thereafter made slightly acid by adding acetic acid and kept aside for a night. The insoluble mineral matters are then filtered and the filtrate is evaporated off giving laevorotatory 7-(p.fluorobenzylamino) 8-methyl nonanoic acid. The yield amounts to 90%. The acid is further recrystallised from acetonitrile, giving crystals melting at 91°-100°.

$\{\alpha\}_{578}^{22} = 5°1$ (C=1% buffer pH 7)

$\{\alpha\}_{365}^{22} = 16.5°$ (C=1% buffer pH 7)

$\{\alpha\}_{578}^{22} = 8.2°$ (C=1% buffer pH 10)

$\{\alpha\}_{365}^{22} = 27.8°$ (C=1% buffer pH 10)

Similarly laevorotatory ethyl esters of 7-(m.methoxy benzylamino) 8-methyl nonanoic acid, of 7-(p.chlorobenzylamino) 8-methyl nonanoic acid, of 7-($\alpha$-methylbenzylamino) 8-methyl nonanoic acid and of 7-($\alpha$-ethyl benzylamino) 8-methyl nonanoic acid are saponified in order to produce the corresponding laevorotatory free acids.

EXAMPLE X

Dextrorotatory 7-(para fluorobenzylamino) 8-methyl nonanoic acid

Step A

From the mother liquors of the step C of example IX they are obtained after evaporation under reduced pressure, conversion into the free base, addition of 1(−) tartaric acid, recovering of the thus precipitated 1(−) tartarate and recrystallisation from ethanol, 30g of the laevorotatory ethyl ester of 7-amino 8-methyl nonanoic acid, 1(−) tartarate the compound melts at 100°-103° C.

$\{\alpha\}_{578} = - 20°$ (C=1% water)

$\{\alpha\}_{365} = - 46.6°$ (C=1% water)

The 1(−) tartarate is converted into the free base (yield 15.4g)

$\{\alpha\}_{578} = - 14.5°$ (C=1% ethanol)

$\{\alpha\}_{365} = - 40.6°$ (C=1% ethanol)

Step B

Using the procedure of step E of Example IX dextro rotator ethyl ester of 7-(p.fluorobenzylamino) 8-methyl nonanoic acid is obtained with a yield of 82%—BP 140°-141° / 0.08 mm $\{\alpha\}_{578}^{22} = + 3.6°$ (C=1% ethanol)

$\{\alpha\}_{365}^{22} = + 16.6°$ (C=1% ethanol)

Step C

Using the procedure of step F of example IX dextro rotatory 7-(p.fluorobenzylamino) 8-methyl nonanoic acid is obtained with a yield of 90%. It melts at 91°–99°

$\{\alpha\}_{578}^{22} = + 5\%$ (C=1% buffer pH 7)
$\{\alpha\}_{365}^{22} = + 15.7°$ (C=1% buffer pH 7)
$\{\alpha\}_{578}^{22} = + 7.9°$ (C=1% buffer pH[10])
$\{\alpha\}_{365}^{22} = + 26.9°$ (C=1% buffer pH10)

EXAMPLE XI dl 9-(para fluorobenzylamino) 10-methyl undecanoic acid

Using the procedure of example I step D and starting from 9-oxo 10-methyl undecanoic acid and para fluorobenzylamine then hydrogenating in the presence of a platinum catalyst dl 9-(para fluorobenzylamino) 10-methyl undecanoic acid is obtained melting at 78°–82° after recrystallisation from acetonitrile.

This compound is freely soluble in aqueous hydrochloric acid solutions.

| Analysis $C_{19}H_{30}FNO_2 = 323,51$ | | | |
|---|---|---|---|
| | C | H | N% |
| Calculated | 70.54 | 9.34 | 4.33 |
| Found | 70.61 | 9.08 | 4.40 |

The starting 9-oxo 10-methyl undecanoic acid is prepared according to the method described by S Akiya Journal Pharm. Soc. Jap. 76,1401-2 (1956).

EXAMPLE XII dl 8-parafluorobenzylamino 9-methyl decanoic acid

Using the procedure exemplified in example I step D and starting from 8-oxo 9-methyl decanoic acid and para-fluorobenzylamine, dl 8-(para fluorobenzylamino) 9-methyl decanoic acid is obtained.

It melts after recrystallisation from acetonitrile at 110°–114°.

| Analysis $C_{18}H_{28}FNO_2 = 309.43$ | | | |
|---|---|---|---|
| | C | H | N% |
| Calculated | 69.87 | 9.12 | 4.53 |
| Found | 70.38 | 8.90 | 4.80 |

The starting material 8-oxo 9-methyl decanoic acid is obtained according to a method similar to that described by S Akiya Journal Pharm. Soc. Jap. 76,1401-2 (1956).

EXAMPLE XIII dl-6-(p.fluorobenzylamino)-7-methyl-N,N-dimethyloctanamide 14 g of dl 6-(p.fluorobenzylamino)-7-methyloctanoic acid are dissolved in 380 ml hexamethyl phosphoramide and cooled to about 0°. To this solution 3 ml of freshly distilled thionyl chloride are added dropwise. The mixture is stirred and cooled for 4 hours and then 8 g dimethylamine in 20 ml hexamethyl phosphoramide are added. The reaction medium is stirred overnight at room temperature, and then diluted with ethyl ether. 6-(p.fluorobenzylamino)-7-methyl-N,N-dimethyloctanamide (hydrochloride) begins to precipitate. The crystalline mixture is allowed to stand for 4 hours in the refrigerator. The crystals are then filtered, dried, washed with ether and dried again. The pure hydrochloride is obtained by recrystallisation from ethanol. It is converted into the base by dissolving it in water and alkalizing the solution by adding sodium carbonate. The free base is decanted, washed with water and distilled. It boils at 178°–182° under 0.1 mm Hg.

$n_D^{21} = 1.5070$

EXAMPLE XIV dl-6-(p.fluorobenzylamino)-7-methyl-N-methyl-octanamide

Using the procedure described in Example XII the title compound is obtained. It boils at 180°–190° under 0.1 mm Hg.

EXAMPLE XV dl-7-(p.fluorobenzylamino-8-methylnonanamide

Using the procedure described in Example XII and starting from 7-(p.fluorobenzylamino)-8-methylnonanoic acid, 7-(p.fluorobenzylamino)-8-methylnonanamide is obtained as a liquid boiling at 198°–204° under 0.01 mm Hg.

$n_D^{26} = 1.5098$

EXAMPLE XVI dl-N-[6-(p.fluorobenzylamino)-7-methyloctanoyl]-morpholine 9 g of ethyl 6-(p.fluorobenzylamino)-7-methyloctanoate are dissolved in 50 ml tetrahydrofuran and 0.5 g dry sodium methylate are added while stirring. When the suspension appears homogeneous, the suspension is heated to about 50° and progressively a solution of 5 ml morpholine in 25 ml tetrahydrofuran is added. Heating is maintained for 4 hours, then the resulting ethanol is distilled off at reflux temperature. The mixture is then diluted with an equal volume of dilute acetic acid. The cloudy suspension is extracted three times with isopropyl ether, the organic phases are united, washed with water, dried over sodium sulphate and filtered. The solution is evaporated giving a dry residue of N-[6-(p.fluorobenzylamino)-7-methyl-octanoyl]-

EXAMPLE XVII dextro-rotatory 7-(p.fluorobenzylamino)-8-methyl-N-(triallylmethyl)-nonanamide Using the procedure described in Example XVI and starting from 16 g of the ethyl ester of dextro-rotatory 7-(p.fluorobenzylamino)-8-methylnonanoic acid and 8 g triallylmethylamine, dextro-rotatory 7-(p.fluorobenzylamino)-8-methyl-N-(triallylmethyl)-nonanamide is obtained.

EXAMPLE XVIII dl 2,8-dimethyl 7-(p,fluoroebenzylamine)-N-(hexamethlene)-nonanamide 3.09 g of dl 2,8-dimethyl 7-(p.fluorobenzylamino)-nonanoic acid (mixture of α and β isomers) are dissolved in 50 ml acetone. A solution of 7.9 g triethylamine in 20 ml acetone is added and the mixture is cooled to 5°. A solution of 6.8 g ethyl chloroformate in 25 ml acetone is added portionwise while stirring and keeping the temperature at about 5°. The whole mixture is then allowed to warm to ambient temperature, kept aside for 40 minutes and then filtered. The filtrate is added to a solution of hexamethyleneimine in 25 ml acetone and the mixture is kept at about 10° for 18 hours. The solvent is then evaporated off; the dry residue is taken up in a mixture of 100 ml ether and 10 ml water. The organic phase is separated, washed with an aqueous solution of sodium carbonate, then with water, dried over sodium sulphate, filtered and the solvent is distilled off. The compound is crystallized from a mixture of water and acetone and 4.87 g of dl 2,8-dimethyl 7-(p.fluorobenzylamino)-N-(hexamethylene)-nonanamide is obtained.

EXAMPLE XIX

[dl-7-(N-methyl-p.fluorobenzylamino)-8-methyl-N-($\beta$-methylphenethyl)-nonanamide]

Step A

Starting from 7-(p.fluorobenzylamino)-nonanoic acid and formaldehyde, the N-methylene derivative is obtained which is reduced with hydrogen in the presence of a platinum dioxide catalyst to form dl 7-(N-methyl-p.fluorobenzylamino) 8-methylnonanoic acid isolated as the sodium salt which melts above 260° (dec.).

| Analysis $C_{18}H_{27}FN\ NaO_2 = 331.40$ | | | |
|---|---|---|---|
| | C | H | N% |
| Calculated | 65.23 | 8.21 | 4.23 |
| Found | 65.05 | 8.15 | 4.21 |

Step B

Ethyl dl 7-(N-methyl-p-fluorobenzylamino)-8-methylnonanoate 3.31 g of sodium dl 7-(N-methyl-p-fluorobenzylamino)-8-methylnonanoate are dissolved in 25 ml water, 100 ml ethanol and 7.5 ml sulphuric acid are added and the whole mixture is heated to reflux for 3 hours. The solvent is then distilled off and the oily residue purified by fractional distillation. The ethyl ester is a liquid distillating at 151°–153° under 0.01 mm Hg. The yield amounts to 43%.

Step C 3.70 g of ethyl dl 7-(N-methyl-p-fluorobenzylamino)-8-methylnonanoate are dissolved in 40 ml tetrahydrofuran, 0.5 g sodium terbutylate are added. The mixture is heated to reflux and 1.5 g of $\beta$-methyl-phenethylamine in 20 ml tetrahydrofuran are added to this suspension. After 2 hours heating, the solvent is evaporated off under reduced pressure. The residue is taken in with 20 ml dilute acetic acid. After extraction with isopropyl ether, the solution is washed three times with a saturated solution of sodium bicarbonate and then with water and dried over magnesium sulphate and the solvent is evaporated off. dl-7-(N-methyl-p-fluorobenzylamino)-8-methyl-N-($\beta$-methylphenethyl)-nonanamide is recovered and recrystallized from ethyl acetate. The pure compound melts at 74°–76°.

EXAMPLE XX dl 7-(m-trifluoromethylbenzylamino)-8-methylnonanoylmorpholine

Step A

Ethyl dl-7-(m-trifluoromethylbenzylamino)-8-methylnonanoate 60 g of ethyl dl 7-amino-8-methylnonanoate are dissolved in 50 ml ethanol and 12 g of trifluoromethylbenzaldehyde is 142°–added portionwise while stirring. The mixture is heated at reflux for 1½ hours and then allowed to cool to room temperature. To this solution 10 g triethylamine and 0.5 g platinum oxide are added and the mixture is hydrogenated while stirring and heating at 60° for 2 hours. The catalyst is then removed, and washed many times with the solvent. The ethanolic solutions are united and the ethanol is evaporated off. The dry crystalline residue is recrystallized from isopropyl ether and provides a yield of 86 % of ethyl dl 7-(m-trifluoromethylbenzylamino)-8-methylnonanoate which distills at 141°–142° under 0.01 mm Hg.

Step B dl-7-(m-trifluoromethylbenzylamino)-8-methyl-nonanoylmorpholine

Using the procedure described in Example XVI and starting from 3.70 g of ethyl 7-(m-trifluoromethylbenzylamino)-8-methylnonanoate and 5 ml morpholine in 40 ml tetrahydrofuran, 2.85 g of 7-(m-trifluoromethylbenzylamino)-8-methylnonanoylmorpholine are recovered as a liquid.

The 7-(m-trifluoromethylbenzylamino)-8-methyl-nonanoylmorpholine is taken up in 40 ml ethanol and a solution of 2.9 g malic acid in 20 ml ethanol is added. Crystallization of the malate is initiated by scratching and the mixture is then kept aside in a cool place for 12 hours. The precipitate is filterd off, washed with few ml of cold ethanol and dried in vacuo.

dl-7-(m-trifluoromethylbenzylamino)-8-methyl-nonanoylmorpholine, malate melts at above 250° C.

EXAMPLE

Pharmacological Study of the Compounds of the Invention (a) acute toxicity

The compounds of the invention have been tested for acute toxicity on lots of mice (C.C. strain) weighing about 20g. Increasing dosages have been administered through intraperitoneal way or oral way. The animals are kept under survey for 8 days and the deaths, if any, are numbered. The average lethal dosis (LD 50) is determined by calculation according to the method of Wilcox and Lichtfield. By intraperitoneal way the $LD_{50}$ rang from 50 to 200mg kg and by oral way from 100 to 300mg/kg and predominantly from 100 to 200mg/kg per oral way.

(b) effects on the Central Nervous System in the mice

The first active dosis usually induce a slight decrease in the motility and the muscular tone of the animals. Increasing dosis provoke convulsions, mydriasis, tremor and increase of the respiration rythm. There are not any toxic symptom, neither state of depression nor state of hyper excitability.

(c) Activating effect on the somaesthesic pathway. (wet Dog skakes test)

The compounds have been tested on male rats weighing about 150 g. Each batch of rats received by intraperitoneal way of dosis of one compound of the invention, but one which received only the solvent. The number of thus produced shakings is determined on each lot by portions of 5 minutes, during 30 minutes after the injection and represents the addition of all the individual shakings of the batch.

The expressed results are proportional to the injected dosis.

The compounds have been tested at dosis ranging from 6.5 mg/kg to 50 mg/kg and the number of shakes ranges from 50 to 175 at 25 mg/kg. and up to 120 at 50 mg/kg.

Moreover for dl 2,8-dimethyl 7-(p. fluorobenzylamino) nonanoic acid which appears as one of the most active compounds on this test, very low dosis have been tested and the following results have been obtained:

at 500 μg/kg 75
at 1 mg/kg 82
at 6 mg25/kg 145
at 12 mg5/kg 192
at 25 mg/kg 176

(d) Inhibition of the aggressivity

This test has been performed using the procedure of isolating a single mouse (C.D. strain) in a cage or a male rat (Long Evans strain) after having submitted to ablation of the olfactive bulbs according to the method described by L. Valzelli Agressive Behaviour 1969 p. 70–76, Excerpta Medica Foundation (Amsterdam) and by P. Karli, M. Vergnes and F. Didiergeorges Agressive Behaviour 1969 p. 47–55.

In the mice the compounds of the invention at a dosis from 10 to 50 mg/kg by intraperitoneal route decreases from 20 to 45% the number of fightings and reduce the score of aggressivity.

In the rat increasing dosis from 6,25 to 50 mg/kg by intraperitoneal route decrease progressively the number of agressive animals from about 100% (controls) to about 40% of the animals.

The inhibiting effect of the fightings in the mice and total reduction of aggressivity in a very high percentage of treated lots in the rats did not are followed with side-effects such as hyperactivity or depression state in the treated animals.

What we claim is:

1. A benzylamino alkanoic acid of the formula $I_A$

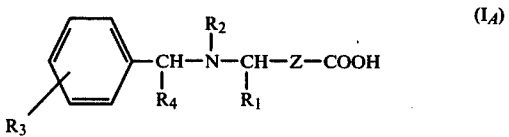

in which
$R_1$ is an alkyl group having from 3 to 6 carbon atoms, each of $R_2$ and $R_4$ is a hydrogen atom or a lower alkyl group,
$R_3$ is a hydrogen atom a halogen atom or a lower alkoxy, trifluoromethyl, trifluoromethoxy, acetylamino, sulfamido, lower alkylaminosulphonyl, dilower alkylaminosulphonyl, cyano or lower acyl group, and
Z is alkylene of 4 to 10 carbon atoms, any one of said carbon atoms being substituted by one or two members of the group consisting of methyl and ethyl.

2. A compound of the formula I′

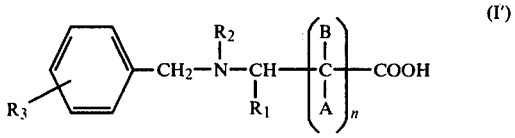

wherein $R_1$ represents a lower alkyl radical having from 3 to 6 carbon atoms in a straight or branched chain,
$R_2$ represents a hydrogen atom or a lower alkyl radical having from 1 to 5 carbon atoms in a straight or branched chain,
$R_3$ represents a hydrogen atom, a lower alkoxy radical or a trifluoromethyl radical, or a halogen atom,
A and B, which may be the same or different, each represents a hydrogen atom, a methyl radical or an ethyl radical, and
n is an integer from 4 to 10
according to claim 1.

3. dl 7-(p.fluorobenzylamino) 9-methyldecanoic acid and its optically-active isomers according to claim 1.

4. dl 7-(p.fluorobenzylamino) 10-methylundecanoic acid, according to claim 1.

5. dl 7-(p.fluorobenzylamino) 9,9-dimethyldecanoic acid, according to claim 1.

6. dl 7-(p.fluorobenzylamino) 8-methylnonanoic acid, according to claim 1.

7. dl 4,4-dimethyl 7-(p.fluorobenzylamino) 8-methylnonanoic acid, according to claim 1.

8. dl 8-(p.fluorobenzylamino) 9-methyl decanoic acid, according to claim 1.

9. dl 9-(p.fluorobenzylamino) 10-methyl undecanoic acid, according to claim 1.

10. dl 2,8-dimethyl 7-(p.fluorobenzylamino) nonanoic acid, according to claim 1.

11. A salt of a compound of claim 1 with a mineral or organic base.

12. A pharmaceutical composition for inhibition of aggressive activity comprising at least one compound of claim 1 or a salt thereof, in admixture or conjunction with a pharmaceutically suitable carrier.

13. A pharmaceutical composition according to claim 12 wherein the amount of active ingredients ranges from 10 to 500 mg per unit dosage.

14. A method of inhibiting aggressive conditions in human or domestic animal patients which consists in administering to said patients subject to said aggressive conditions a sufficient amount of a compound of claim 1 sufficient to be effective in inhibiting said aggressive conditions.

15. The method of claim 14 wherein the effective amount ranges between 0.8 to 33 mg/kilogram body weight of patient per day.

16. An ester of the formula $I_C$

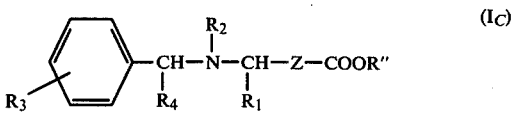

in which
$R_1$ is an alkyl group having from 3 to 6 carbon atoms, each of $R_2$ and $R_4$ is a hydrogen atom or a lower alkyl group,
$R_3$ is a hydrogen atom a halogen atom or a lower alkoxy, trifluoromethyl, trifluoromethoxy, acetylamino, sulfamido, lower alkylaminosulphonyl, dilower alkylaminosulphonyl, cyano or lower acyl group,
Z is alkylene of 4 to 10 carbon atoms, any one of said carbon atoms being substituted by one or two members of the group consisting of methyl and ethyl,
and R″ is a lower alkyl group, a phenyl group, or a substituted phenyl group.

* * * * *